United States Patent [19]

Doppelt

[11] Patent Number: 6,130,345
[45] Date of Patent: Oct. 10, 2000

[54] COPPER (1) PRECURSORS FOR CHEMICAL DEPOSIT IN GAS PHASE OF METALLIC COPPER

[75] Inventor: Pascal Doppelt, Paris Cedex, France

[73] Assignee: Centre National de la Recherche Scientifique, Paris Cedex, France

[21] Appl. No.: 09/380,948

[22] PCT Filed: Mar. 13, 1998

[86] PCT No.: PCT/FR98/00518

§ 371 Date: Dec. 15, 1999

§ 102(e) Date: Dec. 15, 1999

[87] PCT Pub. No.: WO98/40387

PCT Pub. Date: Sep. 17, 1998

[30] Foreign Application Priority Data

Mar. 13, 1997 [FR] France ................................. 97/03029

[51] Int. Cl.[7] ................................ C07F 1/08; C23C 16/00
[52] U.S. Cl. ........................ 556/12; 356/117; 427/248.1; 427/587
[58] Field of Search ................... 556/117, 12; 427/248.1, 427/587

[56] References Cited

U.S. PATENT DOCUMENTS 5,144,049  9/1992  Norman et al. ............................ 556/12
5,663,391  9/1997  Machida et al. ........................... 556/12

FOREIGN PATENT DOCUMENTS

0070638 B1  3/1985  European Pat. Off. .

*Primary Examiner*—Porfirio Nazario-Gonzalez
*Attorney, Agent, or Firm*—Mintz, Levin, Cohn, Ferris, Glovsky & Popeo, P.C.; Ivor R. Elrifi; John T. Prince

[57] ABSTRACT

The invention concerns complex compounds of oxidised copper (+1) stabilised by a ligand for the gas phase chemical deposit of copper in which copper is coordinated with a β-diketonate and the ligand is an alkyne of which the triple bond is partially deactivated by one or two groups slightly attracting the electrons by said alkyne.

14 Claims, No Drawings

COPPER (1) PRECURSORS FOR CHEMICAL DEPOSIT IN GAS PHASE OF METALLIC COPPER

The present invention relates to the chemical deposit method in gas phase of pure metals such as copper and silver, in the electronics industry, for the production of integrated circuits. This method, called CVD for "Chemical Vapor Deposition" is widely used to produce, from precursors of said metals in oxidised form (+1), the interconnections and metallisation of integrated circuits measuring 0.25 μm or less.

Numerous copper precursors are known in the prior art for the fabrication of films made up of said pure metal. The most promising precursors are complex compounds of oxidised copper (+1) stabilised by a ligand in which the copper is compounded with a β-diketonate having the following general formula:

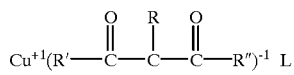

in which R, R' and R", identical or different, are chosen from among a hydrogen atom, a halogen atom such as fluorine, a lower alkyl optionally substituted by one or more fluorine atoms.

Preferred complexes are those in which R is a hydrogen atom and R' and R" are perfluorine alkyls, advantageously —$CF_3$ groups meeting the following structural formula:

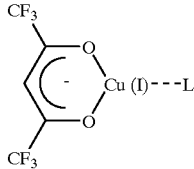

Such complexes and the way they are used in the CVD method are, for example, described in U.S. Pat. Nos. 5,085,731, 5,096,737, 5,098,516, 5,144,049, 5,187,300 whose teaching on the CVD method is incorporated herein by reference.

The work conducted on these precursors demonstrates that their molecular structure is decisive for the reproducible production of films of good quality (P. Doppelt and T. H. Baum, MRS Bull. XIX(8) 41, 1994). However, the electronics industry does not have available an ideal precursor for the reproducible fabrication of electronic circuits containing thin copper films to enable defect-free filling of vertical lines and interconnections that offers low resistivity and good long term thermal stability.

As reported in the above-mentioned patents, the formation of metallic copper results from the dismutation of two copper molecules (I) on a surface heated to a temperature close to 200° C. in accordance with the following reaction:

2Cu(I)(*hfac*)L→Cu(II)(*hfac*)2+Cu(O)+2L

The nature of the Lewis base L, also called hereafter the ligand, only slightly influences the nature of the copper films obtained by CVD. Copper films are generally very pure, free of carbon or oxygen atoms (less than 1%), and resistivity in the region of 1.8 μΩ is frequently found in copper films obtained by CVD; this value is very close to the one found in solid copper (1.67 μΩ.cm). On the other hand, the nature of ligand L determines the volatility of the complex and consequently the rate of deposit of the copper obtained.

In the prior art, more than 80 copper complexes (I) (hfac) are known which have been tested for the CVD of copper, such as for example:

- carbon monoxide, isonitrile, unsaturated hydrocarbon ligands, comprising at least one non-aromatic insaturation cited in U.S. Pat. No. 5,098,516;
- alkynes and acetylene derivatives, dienes, olefins and phosphines, cited in U.S. Pat. No. 5,096,737;
- the compounds cited in U.S. Pat. No. 5,144,049 meeting the formula:

$C(R^4)(R^5)=C(R^5)Si(R^6)_3$ in which $R^4$, $R^5$ and $R^6$ are hydrogen atoms or lower alkyls at $C_1$ to $C_8$.
- the compounds cited in U.S. Pat. No. 5,187,300 meeting the formula:

R4C—C≡Si(R⁵)3 in which $R^4$ and $R^5$ are lower alkyls at $C_1$ to $C_8$.

The three copper precursors for CVD, liquid at ambient temperature, given in Table I below have been the subject of particular study:

TABLE I

| Precursors | Volatility |
|---|---|
| 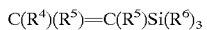 | Very volatile up to 200 nm/min ($H_2O$) |
|  | Scarcely volatile: 140 nm/min |
| 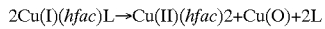 | Very volatile up to 400 nm/min. Formation of a less volatile secondary product |

Among the latter, the (3-hexyne) Cu(hfac) complex is the one which gives the highest growth rate. On the other hand, it has recently been shown that it leads to the formation of dinuclear complexes which form a major obstacle to its use (P. Doppelt and T. H. Baum, Journal of Organometallic Chemistry 517, 53–62, 1996).

In order to remedy this disadvantage, the inventors have examined electronic phenomena related to the formation of dinuclear complexes during the use of a copper complex for CVD stabilised by a ligand made up of an alkyne whether substituted or not. Research work conducted has been able to demonstrate that the formation of these dinuclear species is helped when the alkyne carries electron-donor groups, such as for example the $Si(R)_3$ group described in U.S. Pat. No. 5,187,300.

The present invention sets out precisely to provide a solution to the problem raised by the formation of dinuclear complexes during the use of a copper complex stabilised by a ligand of triple bond carrying type, while maintaining the potentialities of the precursor for CVD. This objective is reached by using ligands in which the triple bond is partially deactivated by one or two groups slightly attracting electrons, such as a double bond or one or two alkoxy groups with the formula $—O—(CH_2)n—CH_3$ in which n is 0 up to the order of 8 and is advantageously a methoxy group ($—O—CH_3$).

The invention therefore relates to organometallic complexes that are liquid volatile or solid with low melting point, also called hereafter copper precursors (I) for gas phase chemical deposit having the general formula (I):

in which R' and R", identical or different, are a lower alkyl optionally substituted by one or more halogen atoms such as fluorine, R is chosen from among a hydrogen atom, a halogen atom such as fluorine, a lower alkyl optionally substituted by one or more halogen atoms such as fluorine, and L represents the stabilising ligand of said complex characterized in that L is an alkyne whose triple bond is partially deactivated by one or two groups slightly attracting the electrons carried by said alkyne.

When L is an alkyne of which the triple bond is partially deactivated by two slightly electron-attracting groups, it is preferred that the latter be arranged either side of said triple bond.

One ligand of the invention meets the following formula (II):

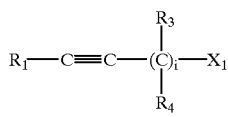

or the following formula (III):

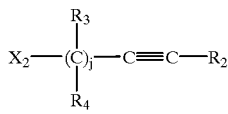

or the following formula (IV):

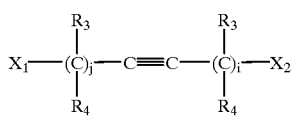

in which $R_1$, $R_2$, $R_3$ and $R_4$, identical or different, are chosen from among a hydrogen atom, a lower alkyl substituted by one or more fluorine atoms, a $—Si(R_5)_3$ group in which $R_5$ is a lower alkyl, i and j are 0 to 3 and $X_1$ and $X_2$, identical or different, represent a group that is slightly electron-attracting.

One first group of preferred ligands of the invention are alkene-ynes, that is to say compounds comprising one or two double bonds and one triple bond. These ligands are those with the formula (II), (III) or (IV) in which $X_1$ and $X_2$ identical or different are radicals with the following formula (V):

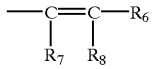

in which $R_6$, $R_7$ and $R_8$ are chosen from among a hydrogen atom, a lower alkyl substituted by one or more fluorine atoms, a $Si(R_5)_3$ group in which $R_5$ is a lower alkyl, or in which $R_6$ and $R_2$ together or $R_6$ and $R_1$ together, or two $R_6$ radicals together, form a group having the formula (VI):

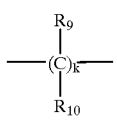

in which $R_9$ and $R_{10}$ are chosen from among a hydrogen atom, a lower alkyl substituted by one or more fluorine atoms, a $Si(R_5)_3$ group in which $R_5$ is a lower alkyl, and k is 1 to 3, such as to form ligands with cyclical formulas, such as for example:

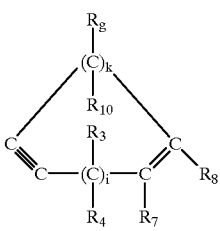

in which $R_3$, $R_4$, $R_6$, $R_7$, $R_8$, $R_9$, $R_{10}$, i and k have the same denotation as in formulas (II), (V) and (VI).

Among the formula (IV) compounds in which $X_1$ and $X_2$ are of formula (V), preference is given to those in which i or j is different from 0, such as to avoid combining of the double bonds and the triple bond.

Among the compounds of formulas (II) or (III), particular preference is given to:

2-methyl-1-hexen-3-yne with the formula:

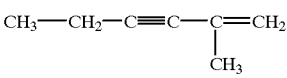

1-hexene-3-yne with the formula:

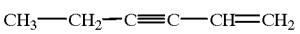

A second group of preferred ligands of the invention are those with formulas (II), (III) or (IV) in which $X_1$ and $X_2$, identical or different, are radicals with the following formula (VII):

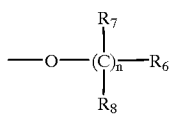

in which $R_6$, $R_7$, $R_8$ have the same denotation as in formula (V) and n is 0 to 8 such that $(C)_n$-$R_6$ remains a lower alkyl.

A third group of ligands of the invention are those comprising both an alkoxy group and a group comprising a double bond each placed either side of the double bond, these ligands meeting formula (IV) in which $X_1$ has the formula (V) and $X_2$ has the formula (VII) or the reverse.

In the above formulas, by lower alkyl is meant more particularly the alkyls at $C_1$ to $C_8$, linear or branched, such as —$CH_3$ or —$C_2H_5$. These may be substituted by one or more fluorine atoms such as the radicals: —$CF_3$, —$C_2F_5$, —$CH_2CF_3$, —$CF_2CH_3$).

Other advantages and characteristics of the invention will become apparent in the following examples relating to the preparation and analysis of copper complexes with the formula:

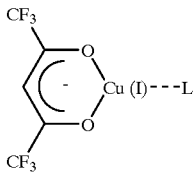

in which L is 2-methyl-1-hexen-3-yne or 1-hexene-3-yne which are compounds whose preparation has already been described in the prior art and which are known in particular as polymerization agents.

EXAMPLE 1

The ligand used in this example is 2-methyl-1-hexen-3-yne that is commercially available. The copper complex was synthesized using a method described in the prior art (P. Doppelt, T. H. Baum and L. Ricard, Inorg. Chem. 35, 1286, 1996). Its characteristics are as follows: Anal. Calculated for $CuC_{12}H_{11}F_6O_2$: C, 39.6; H, 3.05; F, 31.32; Cu, 17.3. Found: C, 40.0; H, 3.10; Cu 17.0. m.p.=15° C. IR (liquid between two NaCl discs): 2983 (f), 2016.3 (f. C≡C), 1671 (m), 1556 (m), 1531 (m), 1490 (s), 1348(f), 1258 (F), 1203 (F), 1147 (F), 1104 (f), 917 (f), 800 (m), 673 (m), 665 (m), 581 (m), $cm^{-1}$. $^1$H NMR (Bruker, 300 Mhz, $CDCl_3$, 20° C.): δ 1.34 (t, 9 Hz, $CH_3$), 2.07 (s, $CH_3$), 2.71 (q, 9 Hz, $CH_2$), 5.33 (s =CH), 5.58 (s, =CH), 6.18 (s, C—H hfac), $^{13}$C NMR: δ 13.74 (s, $CH_3$), 16.24 (s, $CH_3$), 23.73 (s, $CH_2$), 87.68 (s, C—H), 89.90 (s, C≡C), 95.76 (s, C≡C), 117.82 (q, 315 MHz, $CF_3$), 121.54 (s, C≡C), 178.12 (q, 32 Hz, C≈O).

EXAMPLE 2

The ligand used in this example is 1-hexene-3-yne which is not commercially available but whose characteristics are known. This compound was prepared by adapting a method described in the prior art (G. Eglinton and M. C. Whiting, J. Org. Chem. 3650 (1950). The copper complex was synthesized as in example 1, and its characteristics are the following: m.p.=18° C. IR (liquid between two NaCl discs): 2986 (f), 2944 (f), 2885 (rf), 2016.4 (f, C≡C), 1641 (m), 1556 (m), 1531 (m), 1472 (s), 1409 (m), 1348 (f), 1257 (F), 1202 (F), 1147 (F), 1102 (f), 967 (f), 800 (m), 673 (m), 589 (m), $cm^{-1}$. $^1$H NMR (Bruker, 300 MHz, $CDCl_3$, 20° C.): δ 1.37 (t, 7.3 Hz, $CH_3$), 2.67 (qd, 1.5 and 7.5 Hz, $CH_2$), 5.47 (dd, 1.5 and 10.7 Hz, =CHH), 5.8 (dd, 1.5 and 16.9 Hz, =CHH), 6.05 (ddt, 16.9, 1.5 and 10.7 Hz, =CH, 6.15 (s, C—H, hfac), $^{13}$C NMR; δ 13.49 (s, $CH_3$), 16.05 (s, $CH_2$), 83.72 (s, C≡C), 89.77 (s, C—H), 96.15 (s, C≡C), 112.5 (s, =CH), 117.8 (q, 315 Hz, $CF_3$), 121.91 (s, C=C) 178.27 (q, 32 Hz, C=O).

EXAMPLE 3

Analysis of the complexes in examples 1 and 2

With the NMR spectrum of the proton it is possible to determine the stoicheiometry of the complexes by comparing the peak integration of the ligand and of H methine of hexafluoroacethylacetonate; this ratio is definitely 1 which confirms the structure of the complexes given in examples 1 and 2.

The NMR spectra of $^{13}$C lead to asserting that the copper is bound to the triple bond by comparing the peaks of the free ligand and of the chelated ligand. The new complexes of the invention are much more stable than the corresponding complex in which the ligand is 3-hexyne; in the latter case it has been shown that the triple bond is capable of chelating (hfac)CU+ ions to yield a much less stable complex. With the complexes of the invention, however, the triple bond is sufficiently deactivated owing to the combining of two insaturations to prevent the formation of binuclear complexes.

The complexes of examples 1 and 2 are both yellow liquids at ambient temperature. They have been successfully used as precursors to deposit films of metallic copper by CVD. They offer both good volatility, and consequent rapid growth of the copper film, and great stability at evaporation temperature. By way of comparison, for the complex in example 1, the temperature of the bubbler was maintained at 65° C. with no detectable degradation after two periods of 12 hours.

What is claimed is:

1. Complex compound of oxidised copper (+1) stabilised by a ligand for the gas phase chemical deposit of copper having the general formula (I):

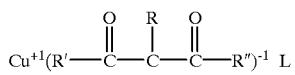

in which R' and R", identical or different, are a lower alkyl, optionally substituted by one or more halogen atoms, R is chosen from among a hydrogen atom, a halogen atom, a lower alkyl optionally substituted by one more halogen atoms, and L represents the ligand stabilising said complex, characterised in that L is an alkyne of which the triple bond is partially deactivated by one or two groups slightly attracting the electrons carried by said alkyne such as to make it incapable of chelating another metal.

2. Complex according to claim 1, characterized in that L is an alkyne of which the triple bond is partially deactivated by two groups slightly attracting electrons arranged either side of said triple bond.

3. Complex according to claim 1, in which R' and R" identical or different, are a lower alkyl, optionally substituted by one or more halogen atoms, wherein the halogen atoms are fluorine atoms.

4. Complex according to claim 1, in which R is chosen from among a halogen atom, wherein the halogen atom is a fluorine atom.

5. Complex according to claim 1, in which R is chosen from among a lower alkyl optionally substituted by one more halogen atoms, wherein the halogen atoms are fluorine atoms.

6. Complex compound of oxidised copper (+1) stabilised by a ligand for the gas phase chemical deposit of copper, characterised in that said ligand L meets the following formula (II):

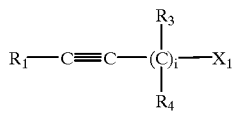

or formula (III) as follows:

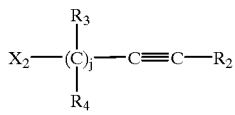

or formula (IV) as follows:

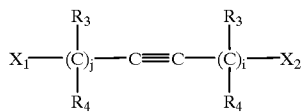

in which $R_1$, $R_2$, $R_3$ and $R_4$, identical or different, are chosen from among a hydrogen atom, a lower alkyl substituted by one or more fluorine atoms, a —Si($R_5$)$_3$ group in which $R_5$ is a lower alkyl, i and j are 0 to 3 and $X_1$ and $X_2$, identical or different, represent a group that is slightly electron-attracting.

7. Complex compound of oxidised copper (+1) stabilised by a ligand for the gas phase chemical deposit of copper according to claim 6, characterized in that said ligand meets one of formulas (II), (III) or (IV) in which $X_1$ and $X_2$, identical or different, are radicals with formula (V) as follows:

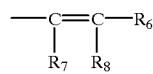

in which $R_6$, $R_7$ and $R_8$ are chosen from among a hydrogen atom, a lower alkyl substituted by one or more fluorine atoms, a Si($R_5$)$_3$ group in which $R_5$ is a lower alkyl, or in which $R_6$ and $R_2$ together or $R_6$ and $R_1$ together, or two $R_6$ radicals together form a group having the following formula (VI):

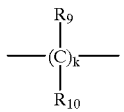

in which $R_9$ and $R_{10}$ are chosen from among a hydrogen atom, a lower alkyl substituted by one or more fluorine atoms, a Si($R_5$)$_3$ group in which $R_5$ is a lower alkyl, and k is 1 to 3 such as to form ligands having cyclical formulas.

8. Complex according to claim 7, characterized in that it meets formula (IV) in which $X_1$ and $X_2$ are of formula (V) and i or j is different from 0.

9. Complex according to claim 7, characterized in that L is 2-methyl-1-hexen-3-yne.

10. Complex according to claim 7, characterized in that L is 1-hexene-3-yne.

11. Complex compound of oxidised copper (+1) stabilised by a ligand for the gas phase chemical deposit of copper according to claim 3, characterized in that said ligand meets one of formulas (II), (III) or (IV) in which $X_1$ and $X_2$, identical or different, are radicals of formula (VII) as follows:

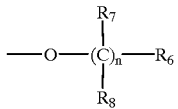

in which $R_6$, $R_7$, $R_8$ have the same denotation as in claim 4, and n is 0 to 8.

12. Complex compound of oxidised copper (+1) stabilised by a ligand for the gas, phase chemical despoit of copper according to claim 6, characterized in that said ligand meets formula (IV) in which $X_1$ and $X_2$ of formulas (V) or (VII) are different.

13. Complex according to any one of claims 6 to 9, characterized in that in formulas (II), (III), (IV), (V), (VI) and (VII) the lower alkyls are chosen from among alkyls at $C_1$ to $C_8$ either linear or branched optionally substituted by one or fluorine atoms.

14. Method for the gas phase chemical deposit of a metallic copper film on a substrate by contact of said substrate with an organometallic copper precursor volatile in gas phase, characterised in that a complex according to any of claims 1 to 9 is used as said precursor.

* * * * *